United States Patent [19]

Tsuda et al.

[11] Patent Number: 4,551,432
[45] Date of Patent: Nov. 5, 1985

[54] *PARACOCCUS DENITRIFICANS*, FUM-14: A FUMARASE OVERPRODUCER

[75] Inventors: Yoshihisa Tsuda, Wilmette; Denise M. Jackson, Chicago, both of Ill.

[73] Assignee: UOP Inc., Des Plaines, Ill.

[21] Appl. No.: 551,646

[22] Filed: Nov. 14, 1983

[51] Int. Cl.$^4$ .......................... C12N 9/88; C12N 1/20; C12P 7/42; C12R 1/01
[52] U.S. Cl. .................................... 435/232; 435/146; 435/253; 435/822
[58] Field of Search ................................ 435/232, 146

[56] References Cited

FOREIGN PATENT DOCUMENTS 56-42589  4/1981  Japan ............................ 435/232

OTHER PUBLICATIONS

American Type Culture Collection (ATCC) Catalog of Strains, 15th ed., 1982, p. 161.

*Primary Examiner*—Lionel M. Shapiro
*Attorney, Agent, or Firm*—Thomas K. McBride; William H. Page, II; Eugene I. Snyder

[57] ABSTRACT

A strain of *Paracoccus denitrificans*, NRRL B-15710, is an overproducer of a fumarase which is readily purified and relatively thermostable. The fumarase so produced converts fumaric acid to L-malic acid without formation of any significant amounts of a coproduct.

1 Claim, No Drawings

PARACOCCUS DENITRIFICANS, FUM-14: A FUMARASE OVERPRODUCER

BACKGROUND OF THE INVENTION

Although acidulants have various functions in food processing and products, their principal role is to adjust the pH of foods, primarily to enhance and to modify flavor, but also to preserve foods. Acidulants are used to add sourness and a desired tartness to many food products. Because of the low pH created when used, food acids can also prevent growth of microorganisms that might cause food to spoil or cause food poisoning or diseases. Through chelation of trace metal ions and/or low pH, acidulants also prevent rancidity and discoloration of foods by functioning as synergists to antioxidants such as BHA, BHT, and ascorbic acid. They also are used as buffers during various stages of food processing as well as in finished products. Food acidulants may also be used for purposes other than imparting flavor or aiding in preservation. They function as melting modifiers for cheese spreads and mixtures used in making hard candy, as gelling agents, and as viscosity modifiers for doughs. The versatility of acidulants will certainly be a factor in their general increased use as food additives in the future.

U.S. markets for food acidulants include carbonated beverages, powdered soft-drink mixes, noncarbonated beverages (e.g., fruit juice drinks), flavored gelatin desserts, jams and jellies, candies, canned fruits and vegetables, pie fillings, yogurts, starch puddings, and wines. Beverages—including liquids and powders—are the largest end use for acids in food products. Acids are used in soft drinks to provide tartness and to modify sweetness, and they are used in canning tomatoes to alter pH in order to optimize heat processing. Properties of the various acids are important to consider for the different applications; in some uses, high solubility is important (e.g., for flavor concentrates), whereas in other uses sourness and speed of solution may be the critical factors (e.g., powdered beverage mixes).

Of all acids used in foods, citric acid is the most widely used. Malic acid generally is recognized as being versatile and a potential competitor with citric acid. Used as a food acidulant in the United States for only about fifteen years, malic acid has made its greatest inroads when new products are developed and when old products need improvement. It has been successful in replacing citric acid, to some degree, in some major uses, such as dry powder mixes and candies. In new products, it is sometimes used in combination with citric acid.

Beverages based on malic acid use 8 to 12% less acidulant by weight, on the average, than beverages using citric acid, with extremes of 5 to 22% less acidulant having been reported. Although the level of acid required for replacement varies with the type of flavor, level of sweetness, and level of carbonation used, there remains a clear economic incentive for replacing citric acid by malic acid.

Malic acid has penetrated some of citric acid's uses in the nectar and diet-drink market; some sugar-free and low-calorie soft-drink producers have switched to malic from citric acid because malic acid masks the off-taste produced by sugar substitutes (e.g., saccharin). Malic acid is used to enhance the flavor in fruit-flavored (especially the berry flavors) carbonated beverages and cream sodas. It is used in beverages by itself and, in some instances, in combination with citric acid. Newly marketed food and beverage products have been (and are expected to continue to be) malic acid's major acidulant growth market. Other carbonated and still beverages, candies, dessert powders, instant tea, syrups, and preserves are targets for growth. It is believed that malic acid's use in fruit drinks, particularly apple and berry flavors, will increase because of the apparent change in consumer preference for beverage flavors; a faster growth rate in consumption of non-cola-flavored beverages compared to cola beverages is foreseen.

Domestic demand for malic acid as a food and beverage acidulant has increased from about 4 million pounds in 1967 to about 11 million pounds in 1979. Domestic production in 1979 was over 15 million pounds, with the difference between production and demand being exported. The average annual growth rate for malic acid has been estimated between 3 and 8% per year.

Malic acid is naturally found in many fruits, such as apples, and is there produced not as a racemate but as L-malic acid. Regulations in most of Western Europe, with the exception of the United Kingdom, Norway, and Denmark, do not permit additives of a synthetic origin in food and beverages. Therefore, racemic malic acid is not allowed in food and beverages except in those countries mentioned. Consequently, there is a great economic incentive for a method of producing L-malic acid relatively inexpensively.

Presently, malic acid is made by hydration of maleic anhydride to afford racemic malic acid. Resolution of the racemate to obtain L-malic acid is expensive, hence its supply remains limited. The demand for L-malic acid remains high, and for the aforementioned reasons the use of malic acid as an acidulant, especially in Europe, undoubtedly would increase were L-malic acid economically competitive with citric acid.

Fumarase is an enzyme which catalyzes the interconversion of fumaric and L-malic acids under mild conditions typical of enzymatic reactions. The invention herein is based on our discovering a bacterial strain which produces a fumarase which can be easily purified, which has substantial thermal stability even at 50° C., which converts fumaric acid to L-malic acid without any other detectable coproducts, and which can be efficiently immobilized. Our discovery thus makes possible a commercially feasible process of making L-malic acid.

In one aspect our invention is a biologically pure culture of a strain of *Paracoccus denitrificans*, FUM-14, NRRL B-15710. In another aspect our invention is a method of producing a fumarase by growing FUM-14 aerobically in a medium containing an assimilable source of carbon, nitrogen, and mineral nutrients, at a temperature from about 20° to about 45° C., and recovering the fumarase produced thereby. In still another aspect our invention is the fumarase produced by *Paracoccus denitrificans* when grown under the aforesaid conditions.

DESCRIPTION OF THE INVENTION

Fumarase is an enzyme found widely in nature which catalyzes the reaction,

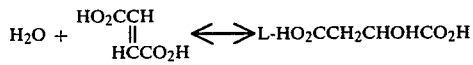

Just as all microorganisms are not equivalent in their ability to produce the enzyme, so are all fumarases not equivalent in their physical-chemical characteristics.

We have discovered a microorganism, isolated from a soil sample, which produces fumarase in greater than usual amounts. Additionally, and equally important from the process standpoint, the fumarase so produced is readily purified, evidences good thermal stability, can be efficiently immobilized, and as an immobilized enzyme converts fumaric to L-malic acid with the equilibrium mixture containing about 80% of the latter, without any substantial amount of byproduct being coproduced. Our discovery makes possible a method of making L-malic acid from fumaric acid using the immobilized fumarase from FUM-14.

The microorganism FUM-14, NRRL B-15710, isolated by the enrichment culture technique from a soil sample, is an overproducer of fumarase. Briefly, a soil sample was grown in a medium containing d, 1-malic acid as the sole carbon source. Successive transfers were made to a similar medium, and after six such transfers the mixed culture was streaked out to isolate single colonies. Colonies were screened for fumarase activity, and FUM-14 was among those exhibiting particularly high fumarase activity.

The enzyme is produced intracellularly and is released into solution by rupture of the cell walls. Such rupture can be performed by mechanical means, such as by homogenization, or by methods such as sonication or digestion with lysing enzymes, such as lysozyme.

After rupture of the cells debris is removed by any suitable means, such as centrifugation; the solution which results is the crude extract of fumarase. It has been found that although the fumarase from this crude extract can be immobilized, other materials in the crude extract lead to decreased activity of the immobilized fumarase. More specifically, although the activity of immobilized fumarase initially increases with increased offering of crude extract, the observed fumarase activity subsequently declines as more crude extract is offered in an attempt to obtain an immobilized fumarase system with greater activity. Thus, it appears necessary to purify, at least partially, the fumarase before its immobilization.

To effect an approximately 30-fold purification of fumarase, the crude extract is first diluted with polyethylene glycol and treated with potassium chloride at a temperature under about 10° C., causing precipitation of unwanted proteins, dialyzing the supernatant from the prior described treatment to remove potassium chloride and other salts, chromatographing the dialyzed solution on a diethylaminoethyl cellulose column, precipitating additional fumarase-inactive protein with a concentrated salt solution at a temperature under 10° C., increasing the salt concentration in the supernatant to precipitate fumarase, and collecting the precipitate formed thereby. The sequence of steps is important; the degree of purification using a different sequence of the above steps will be less than that attained in the given sequence. Partial purification may be effected using chromatographic separation alone.

To the crude extract is added enough polyethylene glycol to form from about a 10 to about a 15% V/V solution, followed by sufficient salt to give from about a 1 to about a 5% W/V solution at a temperature less than about 10° C., preferably less than about 5° C., and most desirably from about 0° to about 2° C. Polyethylene glycol of a molecular weight in the range from about 1000 to about 10,000 can be used satisfactorily, although polyethylene glycol of different molecular weight also may be used but not necessarily with equivalent results. The salt used is typically an alkali metal halide chosen for convenience only, with a concentration of about 3% for potassium chloride being preferred. Addition of both materials is done with stirring and solid is removed by suitable means, such as centrifugation.

The supernatant from the centrifuged material is dialyzed at a pH of about 5 in order to remove the salt used in the aforedescribed precipitation and to adjust the pH before the subsequent treatment. Any solids formed during dialysis are removed and discarded.

The dialysate then is applied to a diethylaminoethyl cellulose column which has been pre-equilibrated with a buffer at a pH of about 5. Elution is performed with a gradient of an alkali halide salt solution. Using potassium chloride as an example a gradient between 0 and 0.4 molar potassium chloride in a suitable buffer at a pH of about 5 may be used. Fractions are assayed for fumarase activity and those containing the enzyme are pooled prior to subsequent salt fractionation.

The enzyme in the pooled fractions is now further purified by salt fractionation. A salt is added to the cooled solution in an amount corresponding to about 25 to about 35% of its saturation point (i.e., the total amount of salt which can be dissolved in the solution). In a preferred embodiment the solution is cooled to a temperature between about 0° and about 10° C., more preferably between about 0° and about 5° C. To be useful the salt must have a solubility such that about a 4 molar solution at 0° C. can be prepared, but is otherwise without limitation. Examples of such salts include ammonium sulfate, ammonium acid sulfate, sodium chloride, potassium acetate, potassium carbonate, and potassium chloride. In another preferred embodiment the salt is an alkali metal or alkaline earth metal sulfate, such as lithium sulfate, sodium sulfate, potassium sulfate, rubidium sulfate, cesium sulfate, and magnesium sulfate. After allowing the solids to precipitate they are removed by suitable means, as by centrifugation, and discarded. At this point an additional amount of salt is dissolved such that the total amount in solution corresponds from about 50 to about 65% of its saturation point, thereby causing precipitation of fumarase. After precipitation is complete the solid containing purified fumarase is collected by suitable means, such as centrifugation.

Salts can be removed from the purified fumarase by any means, such as, for example, by dialysis or gel permeation chromatography. The solid which is collected as described above is redissolved in a buffer at a pH from about 6 to about 8. This enzyme solution then is dialyzed overnight against the same buffer. Purification practiced as described above can lead to enrichment, in terms of units of activity per milligram protein, of over 30-fold with total fumarase recovery in excess of 50%.

Native fumarase from NRRL B-15710 is relatively thermally stable. Although at 55° C. it loses about 80% of its activity in about 30 minutes, it appears to be indefinitely stable at about 40° C. Fumarase activity peaked at a pH of about 7.8, showed half that activity at a pH of about 7.3, and was virtually inactive at a pH of about 6.0. At a pH of about 7.0 the activity of fumarase doubled in going from about 30° C. to about 50° C.

An exceedingly important characteristic of the fumarase of this invention is that it produces L-malic acid from fumaric acid without the formation of any detectable byproducts. That is to say, when the reaction mixture was assayed for product L-malic acid and reactant fumaric acid 100% product balance was obtained.

The examples below are merely illustrative of this invention and do not limit it in any way.

Fumarase activity was assayed spectrophotometrically using a substrate containing 0.05 molar L-malate in 0.1 molar potassium phosphate buffer, pH 7.8. One milliliter of the substrate was preincubated in spectrophotometric cells for 5-10 minutes before addition of enzyme. After enzyme was added the reaction was allowed to proceed for 3 minutes at 40° C. The change in absorbance was determined at 240 nm at 60 second intervals, using an extinction coefficient for fumarate of 2.44 cm$^2$/umole. Enzyme activity was expressed as micromoles of L-malate converted into fumarate per minute.

EXAMPLE 1

A soil sample from the Chicago, Ill. area was incubated in a medium of bacto yeast nitrogen base, 0.5% D-malic acid, 0.5% (NH$_4$)$_2$SO$_4$, and 0.01 M potassium phosphate buffer at pH 7.0 at a temperature of 30° C. for about 16 hours. After that time an inoculum was transferred to a similar medium which was incubated at the same temperature for about the same time. After five transfers the culture was streaked out on Petri plates containing the same medium plus agar. Isolated colonies were screened for fumarase activity, and among those exhibiting high fumarase activity was one originating from FUM-14.

The strain FUM-14 was identified as *Paracoccus denitrificans* based on the carbon utilization data. This strain was composed of gram negative coccal-bacillary cells, arranged singly, in pairs, aggregates or short chains. On nutrient agar after 48 hours this isolate produced two colony types. While both were circular, entire, glistening, flat and creme color, one was opaque and the other translucent. The opaque colony produced the two colony types, hence the culture was considered to be pure, with colonial variation.

The physiology and biochemistry of FUM-14 is summarized below.

| | | | |
|---|---|---|---|
| Motility | − | Urease | − |
| 4° C. growth | − | Nitrate to nitrite | + |
| 25° C. growth | + | Nitrite reduction | + |
| 30° C. growth | + | Nitrite to N$_2$ | + |
| 37° C. growth | + | Hydrogen sulfide (TSI) | − |
| 41° C. growth | − | Lysine decarboxylase | − |
| Fluorescein produced | − | Arginine (Mollers) | − |
| Pyocyanine produced | − | Ornithine decarboxylase | − |
| Pigment produced | − | DL-arginine deamination | − |
| pH 6.0 growth | + | Phenylalanine | − |
| 3% NaCl growth | + | Lecithinase | − |
| 6.5% NaCl growth | − | Phosphatase | − |
| MacConkey agar growth | + | Catalase | + |
| Skim milk agar growth | + | Oxidase | + |
| Aesculin hydrolysis | − | Gluconate oxidation | − |
| Casein hydrolysis | − | Tyrosine degradation | + |
| Starch hydrolysis | − | dl-hydroxybutyrate growth | + |
| Gelatinase | − | Poly-B—Hydroxybutyrate accumulation | + |
| Tween 20 hydrolysis | − | Deoxyribonuclease | + |
| Tween 70 hydrolysis | − | Growth on 0.05% cetrimide | − |
| Indole | − | Growth on acetate as sole carbon source | + |
| Simmons citrate growth | + | Testosterone degradation | − |

Fermentation of FUM-14 after 7 days in the presence of various sugars afforded the following results.

| | | | |
|---|---|---|---|
| Acid from L-arabinose | + | Acid from maltose | + |
| Acid from cellobiose | K | Acid from D-mannitol | + |
| Acid from ethanol | + | Acid from D-mannose | K |
| Acid from D-fructose | + | Acid from L-rhamnose | K |
| Acid from D-glucose aerobically | + | Acid from D-ribose | + |
| Acid from D-glucose anaerobically | − | Acid from sucrose | + |
| Acid from glycerol | + | Acid from trehalose | + |
| Acid from i-inositol | + | Acid from D-xylose | K |
| Acid from lactose | K | Control | K |

+ = acid produced
K = alkaline produced
− = no change

Utilization by FUM-14 of carbohydrates as the sole carbon source after 12 days incubation gave results which are summarized below.

| | | | |
|---|---|---|---|
| L-arabinose | + | M—hydroxybenzoate | + |
| cellobiose | − | 2-ketogluconate | + |
| D-fructose | + | DL-lactate | − |
| D-glucose | + | L-malate | + |
| lactose | − | pelargonate | − |
| maltose | + | propionate | + |
| D-mannitol | + | quinate | − |
| L-rhamnose | − | succinate | + |
| D-ribose | + | L-+-tartrate | − |
| D-sorbitol | + | valerate | − |
| sucrose | + | B—alanine | + |
| trehalose | + | D-A—alanine | + |
| D-xylose | − | betaine | + |
| adonitol | + | glycine | + |
| erythritol | − | L-histidine | + |
| glycerol | + | DL-norleucine | + |
| ethanol | + | L-proline | + |
| geraniol | − | D-tryptophan | − |
| i-inositol | + | L-valine | − |
| sebacic acid | − | DL-arginine | − |
| acetamide | − | benzylamine | + |
| adipate | − | butylamine | + |
| benzoate | − | putrescine | − |
| butyrate | − | mesoconate | − |
| citraconate | − | DL-glycerate | + |
| D-gluconate | + | L-tryptophan | − |
| | | Poly-OH butyrate | + |

EXAMPLE 2

A cell pellet of FUM-14, NRRL B-15710 was resuspended in a small amount of 0.02 M potassium phosphate buffer at a pH of 7.0. To this was added lysozyme and 10$^{-3}$ M ethylenediamine tetracetic acid and the mixture was incubated at 37° C. with agitation until there was visual evidence of cell lysing (ca. 30-60 minutes). After this mixture was chilled in an ice bath cells were further ruptured by sonification using a Branson sonicator, debris was removed by centrifugation at 12,000 rpm for 30 minutes and supernatant was collected by decantation to afford a crude extract of fumarase.

EXAMPLE 3

To a crude extract was added sufficient polyethylene glycol, molecular weight about 6000, to afford an 11.5% V/V solution, to which was further added sufficient potassium chloride to afford a 3.3% W/V solution, the mixture being continually immersed in an ice bath with stirring. When precipitation of solids was complete the mixture was centrifuged at 12,000 rpm for about 20 minutes and the supernatant was collected. This supernatant was then dialyzed overnight against 0.02 M sodium citrate, pH 5.2, to remove potassium chloride and to adjust the pH before chromatography. Any solids which form are removed by centrifugation before chromatography.

A column of diethylaminoethyl cellulose was equilibrated with sodium citrate buffer, 0.02 molar, pH 5.2. Dialysate was applied and the column was washed with the same buffer. Enzyme was then eluted with a gradient of 0 to 0.4 M potassium chloride in the same buffer. Individual tubes were assayed to determine the location of the fumarase activity and the enzyme fractions were pooled.

The pooled fractions were chilled in an ice bath to a temperature less than 5° C. Ammonium sulfate was then added in an amount sufficient to give a 30% saturated solution. When precipitation was complete solids were removed by centrifugation at 18,000 rpm for 15 minutes. The supernatant was decanted, immersed in an ice bath, and additional ammonium sulfate was added thereto in an amount sufficient to afford a 60% saturated solution. Fumarase was precipitated and collected by centrifugation. This solid was redissolved in 0.02 M potassium phosphate buffer, pH 7.0, and dialyzed against the same buffer to remove ammonium sulfate.

The course of purification is summarized in the accompanying table.

TABLE 1

Purification of Fumarase

| Procedure | Volume (mL) | Activity (Units/mL) | Total Units | Protein (mg/mL) | Specific Activity (Units/mg) | Yield (%) |
| --- | --- | --- | --- | --- | --- | --- |
| Crude Extract | 645 | 26.3 | 16,960 | 18.6 | 1.41 | (100) |
| PEG-KCl | 860 | 17.4 | 14,960 | 21.0 | 0.83 | 88.2 |
| After Dialysis pH 5.2 | 1,700 | 8.9 | 15,130 | 4.9 | 1.80 | 89.2 |
| Chromatography | 59 | 177.0 | 10,440 | — | — | 61.6 |
| 30–60% Sat. (NH4)2SO4 | 10 | 916.0 | 9,160 | 29.1 | 31.5 | 53.4 |

As can be seen, a nearly 32-fold purification was achieved with overall recovery of over 53% fumarase.

EXAMPLE 4

The activity of native fumarase was determined by assaying the crude extract for fumarase activity as a function of pH. Results, which are reported as relative activity, are summarized in the accompanying table.

TABLE 2

| pH Profile of Fumarase as Free Enzyme | |
| --- | --- |
| pH | Relative Activity (%) |
| 6.0 | 5 |
| 6.3 | 8 |
| 6.6 | 15 |
| 6.9 | 27 |
| 7.2 | 42 |
| 7.5 | 64 |
| 7.8 | 100 |
| 8.1 | 97 |

EXAMPLE 5

A solution of fumarase, partially purified by chromatography on diethylamino ethyl cellulose, was assayed at various temperatures to determine the temperature-activity profile. Results are summarized in the accompanying table.

TABLE 3

| Effect of Reaction Temperature on Free Fumarase Activity | |
| --- | --- |
| Temperature, °C. | Activity (Units/mL) |
| 22 | 100 |
| 27 | 104 |
| 32 | 108 |
| 37 | 137 |
| 42 | 162 |
| 48 | 207 |
| 55 | 211 |

What is claimed is:

1. A method of producing fumarase comprising growing aerobically *Paracoccus denitrificans*, FUM-14, NRRL B-15710, in a medium containing an assimiliable source of carbon, nitrogen, and mineral nutrients at a temperature from about 20° to about 45° C., and recovering the fumarase produced thereby.

* * * * *